United States Patent [19]

Kauffman

[11] Patent Number: 4,593,113

[45] Date of Patent: Jun. 3, 1986

[54] SYNTHESIS OF TRANSITION METAL DITHIENE COMPLEXES

[75] Inventor: Martin H. Kauffman, Ridgecrest, Calif.

[73] Assignee: The United States of America as represented by the Secretary of the Navy, Washington, D.C.

[21] Appl. No.: 691,591

[22] Filed: Jan. 14, 1985

[51] Int. Cl.$^4$ ............................................. C07F 15/00
[52] U.S. Cl. ...................................... 556/136; 556/146
[58] Field of Search ....................... 260/429 R, 439 R; 556/136, 137, 146

[56] References Cited

U.S. PATENT DOCUMENTS

| | | | |
|---|---|---|---|
| 3,255,195 | 6/1966 | Benson | 260/429.9 X |
| 3,361,777 | 1/1968 | King | 260/429 R |
| 3,397,217 | 8/1968 | Mosby et al. | 260/429.7 X |
| 3,398,167 | 8/1968 | Mahler | 260/429.7 X |
| 3,579,478 | 5/1971 | Dunn et al. | 260/45.75 |
| 3,588,216 | 6/1971 | Bloom | 350/1 |
| 3,743,964 | 7/1973 | Drexhage | 331/94.5 |
| 3,875,199 | 4/1975 | Bloom | 260/429 R |
| 3,894,069 | 7/1975 | Ries | 260/439 R |
| 4,239,843 | 12/1980 | Hara et al. | 430/17 |
| 4,508,655 | 4/1985 | Sasagawa et al. | 260/429 R |

OTHER PUBLICATIONS

Schrauzer et al, J.A.C.S. 87:7, pp. 1483–1489 (1965).
Moeller, Inorganic Chemistry, John Wiley & Sons, Inc., N.Y., pp. 342–344 (1952).
Doolittle, The Technology of Solvents and Plasticizers, John Wiley & Sons, Inc., N.Y., pp. 384–387, 392–403 (1954).
Magde, et al., Chemical Physical Letters, Sep. 15, 1974, vol. 28, No. 2, pp. 263–269.

*Primary Examiner*—Helen M. S. Sneed
*Attorney, Agent, or Firm*—Robert F. Beers; W. Thom Skeer

[57] ABSTRACT

The preparation of transition metal dithiene complexes is disclosed. By the process improved yields of the metal dithiene complexes are realized by substituting highly polar aprotic solvents such as N-methylpyrrolidinone or high boiling point solvents such as diethylene glycol in place of dioxane in the reaction sequence.

10 Claims, No Drawings

SYNTHESIS OF TRANSITION METAL DITHIENE COMPLEXES

BACKGROUND OF THE INVENTION

1. Field of the Invention

The invention relates to infrared (IR) absorption. In particular, this invention relates to dithiene complexes of bivalent transition metals which exhibits infrared absorption characteristics. More specifically, this invention relates to the synthesis of symmetrical transition metal dithiene compounds.

2. Description of the Prior Art

The synthesis of symmetrical and asymmetrical transition metal dithiene compounds are known in the art. A general method of preparing these compounds is disclosed in the article "Picosecond Flash Photolysis and Spectroscopy: Bis-(4-Dimethylaminodithiobenzil) Ni(II), BDN," *Chemical Physics Letters*, Magdi, et al., Vol 28, No. 2, Sept. 15, 1974, pp. 263-269. In addition U.S. Pat. Nos. 3,894,069; 3,743,964 and 3,588,216, disclose the preparation of dithiol metal complexes in yields of from about 10 percent to about 17 percent. However, these references do not disclose the synthesis of the compounds forming the basis of the present invention.

OBJECTS OF THE INVENTION

One of the objects of the present invention is to provide a process for preparing transition metal dithiene compounds which exhibit infrared absorption characteristics.

Another object of the invention is to provide a new and improved process of the type described in which high yields of the metal dithiene compound are obtained.

Yet another object of the invention is to provide a new and improved process for producing dithiene metal complexes of nickel, palladium and platinum for absorbing in the infrared, particularly in the near infrared, for use in the laser and optics arts. These and other objects of the invention will become apparent hereinafter.

SUMMARY OF THE INVENTION

In accordance with the invention, dithiene metal compounds are prepared having the general formula:

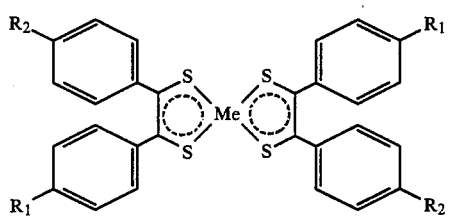

wherein Me is nickel, palladium or platinum, $R_1$ is methoxy ($OCH_3$), and $R_2$ is a dimethylamine group [$N(CH_3)_2$]. These compounds are particularly effective as IR absorbers for 1.06 microns while effectively transparent to light in the visible range, e.g. from about 0.4 to about 0.7 microns.

The following compounds are illustrative of the IR absorbers within the scope of Formula (I):

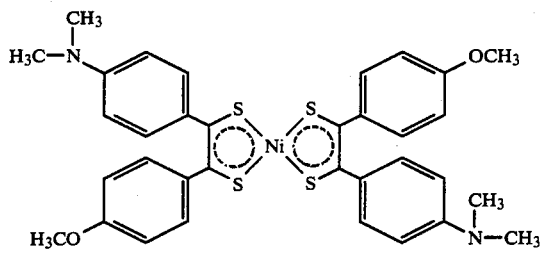

bis(4-Methoxy-4'-Dimethylaminodithiobenzil)Nickel

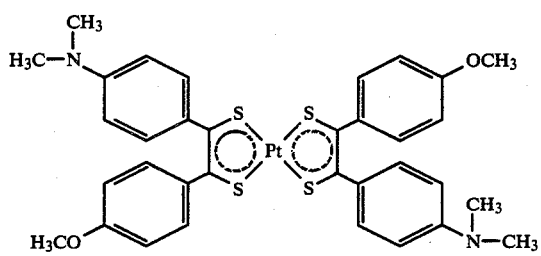

bis(-Methoxy-4'-Dimethylaminodithiobenzil)Platinum

The products of the reaction of dimethylamino derivatives of benzoins with $P_2S_5$ (thiophosphoric esters) have been found to be insoluble in dioxane, the usual reaction medium. In addition, the yields of the nickel, platinum and palladium dithiene complexes are usually only within the range of from about 10 to about 17 percent.

By the new process disclosed herein, improved yields of the aforementioned metal dithiene complexes are realized by substituting highly polar aprotic solvents such as N-methylpyrrolidinone, diglyme (dimethylether of diethlene glycol), methyl sulfolane and thiophene dioxide for dioxane. These solvents were also found to solubilize acceptable quantities of water solutions of the metal salt and were therefore instrumental in bringing about improved yields of the transition metal complexes. It was also shown by experimentation that highly polar aprotic solvents and solvents such as high boiling point ether alcohols, e.g, diethylene glycol or a monoether of diethylene glycol could be used in place of dioxane after the reaction of the $P_2S_5$ with the benzoin compounds thereby enhancing the yield of the metal dithienes.

As previously mentioned the compounds of the present invention may be employed in optical elements. As excellent infrared absorbers, these compounds are effective in concentrations significantly less than that of other compounds such as rare earth oxides presently utilized in glass lenses. Thus these metal dithiene compounds may be employed as infrared absorbers in plastic optical products such as sunglasses or goggles. This could be accomplished by incorporating the compound in chlorinated solvents and forming homogeneous solutions with clear plastic materials like Bisphenol A type polycarbonates, polyacrylates, polystyrene, and the like, and precipitating a molding powder therefrom in a nonsolvent for the complex and the plastic. The resulting plastic optical element may then be fashioned, as known in the art, into lightweight plastic lenses which would protect the wearer from laser radiation in the 1.06 micron wavelength.

DESCRIPTION OF THE PREFERRED EMBODIMENT

The invention is further illustrated by the following examples in which the quantities are stated in parts by weight unless otherwise indicated.

EXAMPLE 1

Into a suitable flask equipped with a stirrer were placed 2.85 grams (0.01 m) of 4-methoxy-4'-dimethylaminobenzoin, 3.5 grams of the phosphorus sulfide $P_2S_5$ and 40 ml dioxane. The mixture was heated to reflux and stirred overnight. A reddish gel-like material containing the thioester derivative of the benzoin insoluble in dioxane precipitated on the vessel wall. After cooling to ambient temperature the dioxane was decanted and the gel-like thioester material was dissolved in about 40 ml of warm N-methylpyrrolidinone. The solution was then filtered and to the supernatant was added 1.46 grams (0.006 gram atoms) $NiCl_2.6H_2O$ in about 4 ml water and the solution was then heated at about 50 degrees C. for about 48 hours. The solution was then poured into 300 ml 95% methanol containing 1.5 ml of 30% $H_2O_2$. The resulting brownish precipitate was filtered and washed with acetone followed by methanol and then air dried. This yielded 2.11 grams of coffee colored powder. The powder was repeatedly extracted with methylene chloride giving a green solution which on evaporation provided 1.16 grams of bis(4-Methoxy-4'-dimethylaminodithiobenzil)Nickel, a yield of 34%.

EXAMPLE 2

To a flask fitted with a stirred was introduced 5.7 grams (0.02 moles) 4-methoxy-4'-dimethylaminobenzoin with stirring into 7 grams (0.031 moles) $P_2S_5$ in 75 ml dioxane which was refluxed for about one hour. A red gel-like material containing the thioester derivatives of the benzoin precipitated on the wall. The flask and contents were then allowed to cool to room temperature and the dioxane decanted off. The solid residue remaining in the flask was dissolved in 75 ml N-methylpyrrolidione and filtered. To the filtrate was added with stirring 2.85 grams (0.012 gram atoms) $NiCl_2.6H_2O$ in 6 ml of water and the contents of the flask heated overnight at from about 40 degrees C. to about 60 degrees C. The resulting reddish solution was cooled to room temperature and poured into 400 ml water containing 3 ml 30% $H_2O_2$, precipitating an amber-colored powder which was filtered and washed successively with water, methanol and acetone. This was followed by vacuum drying giving 7.6 grams of amber-colored powder. Following Soxhlet extraction with toluene 3.05 grams of bis(4-Methoxy-4'dimethylaminodithiobenzil)Nickel resulted, a 44% yield.

EXAMPLE 3

Into a stirrer-equipped flask 2 grams (0.007 m) of 4-methoxy-4'-dimethylaminobenzoin was reacted with 3.5 grams (0.0156 moles) of $P_2S_5$ in 35 ml of the dimethylether of diethleneglycol (diglyme) with heating at about 100° C. After about two hours 3.5 grams (0.014 moles) of $NiCl_2.6H_2O$ in 10 ml water was added. The resulting mixture was heated at about 50 degrees C. with stirring for about 16 hours. After cooling the solution to ambient temperature, 150 ml of acetone was added which precipitated a tarry layer. After decanting the supernatant liquid, 50 ml of methanol was slowly added to the tarry material and a brown powder separated from the oil. The precipitate was washed successively with water, methanol and acetone and then dried. Following extraction of the precipitate with chloroform, 0.5 grams of bis(4-Methoxy-4'-dimethylaminodithiobenzil)Nickel was recovered, a 21% yield.

EXAMPLE 4

The bis(4-Methoxy-4'-Dimethylaminodithiobenzil)-Platinum compound was prepared as in Example 1 using 2.5 grams of 4-methoxy-4'-dimethylaminobenzoin. Following decantation of dioxane, the insoluble wine-colored gel was dissolved in diethylene glycol which is a poor solvent for the desired product. The diethylene glycol solution was filtered to remove excess $P_2S_5$, and an equivalent amount of $K_2PtCl_4$ in 10 ml water was added, and the gel-like material recovered from the evaporated dioxane solution was dissolved in about 5 ml of diethylene glycol and combined with it. This solution was heated for about 24 hours at from about 50 degrees C. to about 60 degrees C. The mixture was then poured into 300 ml of methanol and the precipitate allowed to settle. After filtration, the filtrate was successively washed with methanol, water, and again with methanol. After drying, the solid was Soxhlet extracted with methylene chloride for about two days. On evaporation of the methylene chloride solution, 0.57 grams of the Platinum compound was formed. The solid in the Soxhlet cup was swirled with from about 5 to 10 ml of water to which 3 ml of 30% hydrogen peroxide was added. After about 10 minutes, the solution was filtered off and the solid washed with water and then methanol. The dried material was extracted with methylene chloride. Recrystallization with dichlorobenzene produced an additional 0.2 grams of the platinum compound, a 23.3% yield.

In Examples 1 and 2, the highly polar organic solvents diglyme, diethylene glycol, methyl sulfolane or thiophene dioxide in which an acceptable quantity of the metal chloride reactant remains in solution, may be substituted for methyl pyrrolidinone.

EXAMPLE 5

The palladium compound is prepared as in Example 4 with the substitution of $K_2PdCl_4$ for $K_2PtCl_4$.

While the invention has been particularly shown and described with reference to a preferred embodiment, it will be understood by those skilled in the art that various changes in form and detail may be made therein without departing from the spirit of the invention.

What is claimed is:

1. A process for the synthesis of a transition metal dithiene complex comprising:
   a. reacting a dimethylaminobenzoin with a phosphorus sulfide and dioxane under suitable reaction conditions to produce a dioxane insoluble thiophosphoric ester derivative of the benzoin;
   b. adding excess dioxane and dissolving said thiophosphoric ester derivative in a highly polar aprotic solvent;
   c. reacting said ester derivative dissolved in said aprotic solvent with an aqueous solution of a reactive water soluble ionizable compound of a transition metal complex; and
   d. purifying and recovering the thus prepared metal dithiene complex.

2. A process according to claim 1 in which said dimethylaminobenzoin is 4-methoxy-4'-dimethylaminobenzoin.

3. A process according to claim 1 in which said highly aprotic solvent is selected from the group consisting of N-methyl-pyrrolidinone, diglyme, methyl sulfolane and thiophene dioxide.

4. A process according to claim 1 wherein said reactive water soluble ionizable compound is selected from the group consisting of $NiCl_2$, $K_2PtCl_4$, and $K_2PdCl_4$.

5. A process according to claim 1 in which said phosphorus sulfide is $P_2S_5$.

6. A process for the synthesis of a transition metal dithiene complex comprising:
   a. reacting a dimethylaminobenzoin with a phosphorus sulfide and dioxane under suitable reaction conditions to produce a dioxane insoluble thiophosphoric ester derivative of the benzoin;
   b. adding excess dioxane and dissolving said thiophosphoric ester derivative in a high boiling point glycol solvent;
   c. reacting said ester dissolved in said high boiling glycol solvent with an aqueous solution of a reactive water soluble ionizable compound of a transition metal complex; and
   d. purifying and recovering the thus prepared metal dithiene complex.

7. A process according to claim 6 in which said dimethylaminobenzoin is 4-methoxy-4'-dimethylaminobenzoin.

8. A process according to claim 6 in which said high boiling point glycol is an ether alcohol or a monoether of diethylene glycol.

9. A process according to claim 6 wherein said reactive water soluble ionizable compound is selected from the group consisting of $NiCl_2$, $K_2PtCl_4$, and $K_2PdCl_4$.

10. A process according to claim 6 in which said phosphorus sulfide is $P_2S_5$.

* * * * *